United States Patent
DiMagno et al.

(10) Patent No.: US 10,112,893 B2
(45) Date of Patent: Oct. 30, 2018

(54) GUANIDINIUM COMPOUNDS

(71) Applicant: NUtech Ventures, Lincoln, NE (US)

(72) Inventors: Stephen DiMagno, Chicago, IL (US); Bao Hu, Lincoln, NE (US)

(73) Assignee: NUtech Ventures, Lincoln, NE (US)

( * ) Notice: Subject to any disclaimer, the term of this patent is extended or adjusted under 35 U.S.C. 154(b) by 0 days.

(21) Appl. No.: 15/178,314

(22) Filed: Jun. 9, 2016

(65) Prior Publication Data

US 2017/0001954 A1   Jan. 5, 2017

Related U.S. Application Data

(60) Provisional application No. 62/174,930, filed on Jun. 12, 2015.

(51) Int. Cl.
| | |
|---|---|
| *C07C 279/08* | (2006.01) |
| *C07C 277/08* | (2006.01) |
| *C07C 279/06* | (2006.01) |
| *C07C 309/06* | (2006.01) |
| *C07B 59/00* | (2006.01) |

(52) U.S. Cl.
CPC .......... *C07C 279/08* (2013.01); *C07B 59/001* (2013.01); *C07C 277/08* (2013.01); *C07C 279/06* (2013.01); *C07C 309/06* (2013.01)

(58) Field of Classification Search
None
See application file for complete search history.

(56) References Cited

U.S. PATENT DOCUMENTS

2013/0324718 A1 *  12/2013  DiMagno .............. C07C 269/06
544/131

FOREIGN PATENT DOCUMENTS

| WO | 2013184484 A1 | 12/2013 |
| WO | 2014066772 A1 | 5/2014 |

OTHER PUBLICATIONS

Notification of Transmittal of the International Search Report and the Written Opinion of the International Search Authority for International Application No. PCT/US2016/036741, dated Sep. 15, 2016, 8 pages.

* cited by examiner

*Primary Examiner* — Clinton A Brooks
*Assistant Examiner* — Jennifer C Sawyer
(74) *Attorney, Agent, or Firm* — Wolf, Greenfield & Sacks, P.C.

(57) ABSTRACT

The present application provides, inter alia, chemical compounds useful as synthesis intermediates, said compounds comprising one or more guanidinium moieties and a hypervalent iodine atom. Methods for making these compounds are also provided.

15 Claims, 4 Drawing Sheets

GUANIDINIUM COMPOUNDS

RELATED APPLICATION

This application claims priority to U.S. Provisional Application No. 62/174,930, filed on Jun. 12, 2015, the content of which is incorporated herein by reference in its entirety.

STATEMENT OF FEDERALLY SPONSORED RESEARCH

This invention was made with government support under Grant No. R01EB015536 awarded by the National Institute of Biomedical Imaging and Bioengineering and National Institutes of Health. The Government has certain rights in the invention.

TECHNICAL FIELD

This disclosure relates to chemical compounds comprising one or more guanidinium moieties and a hypervalent iodine atom, and processes for making these compounds.

BACKGROUND

The compounds MIBG (Iobengane, meta-iodobenzylguanidine or mIBG), and the astatine analog MABG (meta-astatinobenzylguanidine), are used diagnostically to detect a variety of disorders. The compounds comprise a radioactive iodine or astatine atom, and a protonated guanidine (i.e., guanidinium) moiety. Available synthesis methods for the preparation of MIBG and MABG require protection of the guanidine moiety during the synthesis steps used to attach the radioactive iodine or astatine atom. Subsequent deprotection of the guanidine moiety results in the formation of radioactive byproducts, impurities and solvent waste. Moreover, radioactive halogen atoms have short half-lives, and deprotection and purification procedures consume much of the limited time within which the compounds are useful. There remains a need for intermediates and methods for the efficient synthesis of MIBG, MABG, and related compounds, said intermediates and methods avoiding the use of guanidine protecting groups.

SUMMARY

Accordingly, the present disclosure provides chemical compounds useful as intermediates in the synthesis of MIBG, MABG, and related compounds having one or more guanidine or guanidinium groups, wherein the guanidine or guanidinium groups of said compounds are not protected (referred to as "compounds of the invention"). Surprisingly, it has been discovered that protection of the guanidine or guanidinium groups of the compounds of the invention is not required during the synthesis of the compounds or during the conversion of the compounds of the invention into MIBG, MABG, or related compounds.

The compounds of the invention, and related methods, are advantageous over the prior art, at least because they permit the more rapid and efficient synthesis of compounds having short radioisotopic half-lives, thereby maximizing the lifetime of the radio-labelled products. Furthermore, the compounds of the invention and related methods avoid the formation of radioactive byproducts and waste associated with deprotection procedures.

In a first aspect, provided herein is a compound of formula (I):

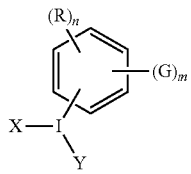
(I)

wherein: G is -L-NH—C(—NH$_2$)(=NH$_2$)Y; R is independently selected from the group consisting of halogen, C$_1$-C$_6$ alkyl and C$_1$-C$_6$ alkyloxy; X is selected from the group consisting of optionally substituted aryl, optionally substituted heteroaryl, and stabilized enolate; Y is absent or is an anion selected from the group consisting of bicarbonate, halide, aryl carboxylate, alkyl carboxylate, phosphate, phosphonate, phosphonite, azide, thiocyanate, cyanate, phenoxide, arylsulfonate, alkylsulfonate, trifluoromethanesulfonate, thiolate, and stabilized enolate; L is absent or is an optionally substituted linker selected from the group consisting of alkyl, alkenyl, heteroalkyl, alkylcarbonyl, heteroalkylcarbonyl, cycloalkyl, heterocycloalkyl, aryl, and heteroaryl; n is 0-4; and m is 1-2.

In a second aspect, provided herein is a method of making a compound of formula (I):

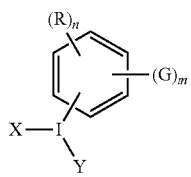
(I)

the method comprising:
Step 1: Reacting a Compound of Formula (Ia):

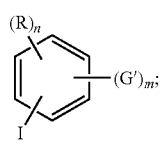
(Ia)

wherein G' is -L-NH—C(—NH$_2$)(=NH) or a salt thereof; and R is independently selected from the group consisting of halogen, C$_1$-C$_6$ alkyl and C$_1$-C$_6$ alkyloxy;

with (i) a compound selected from the group consisting of (1-chloromethyl-4-fluoro-1,4-diazoniabicyclo[2.2.2]octane) bis(tetrafluoroborate), (1-fluoro-4-methyl-1,4-diazoniabicyclo[2.2.2]octane) bis(tetrafluoroborate), and optionally substituted N-fluoropyridinium tetrafluoroborate;

and (ii) a compound of formula:

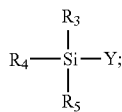

wherein R$_3$, R$_4$ and R$_5$ are optionally substituted substituents independently selected from the group consisting of alkyl, heteroalkyl, alkylaryl, aryl and heteroaryl; and wherein Y is an anion selected from the group consisting of halide, aryl carboxylate, alkyl carboxylate, phosphate, phosphonate, phosphonite, azide, thiocyanate, cyanate, phenoxide, arylsulfonate, alkylsulfonate, trifluoromethanesulfonate, thiolate, and stabilized enolate; to obtain a compound of formula (Ib):

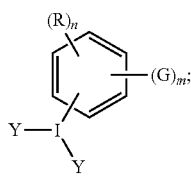

(Ib)

and

Step 2: Reacting the Compound of Formula (Ib) with a Compound of Formula:

X-M¹ wherein X is selected from the group consisting of optionally substituted aryl, optionally substituted heteroaryl, and stabilized enolate; and $M^1$ is a borate, stannane, silane, or zinc moiety; to obtain a compound of formula (I).

In a third aspect, provided herein is a method of making a compound of formula (X):

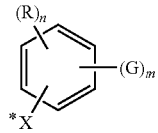

(X)

wherein *X is selected from the group consisting of I-123, I-124, I-125, I-131, At-210 and At-211; and G and R are defined as above; the method comprising the step of reacting a compound of formula (I) with a source of I-123, I-124, I-125, I-131, At-210 and At-211 such that the compound of formula (X) is formed.

DETAILED DESCRIPTION

Compositions

Figure 1:
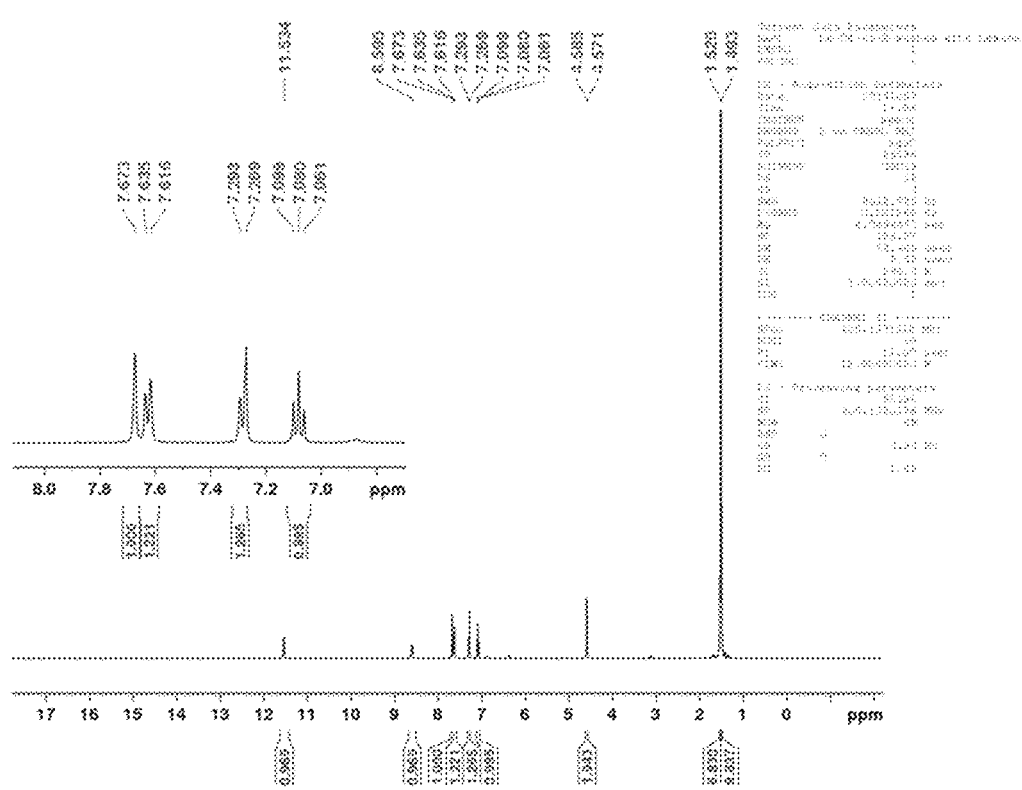
FIG. 1 depicts the 1HNMR spectrum of compound 2.
Figure 2:
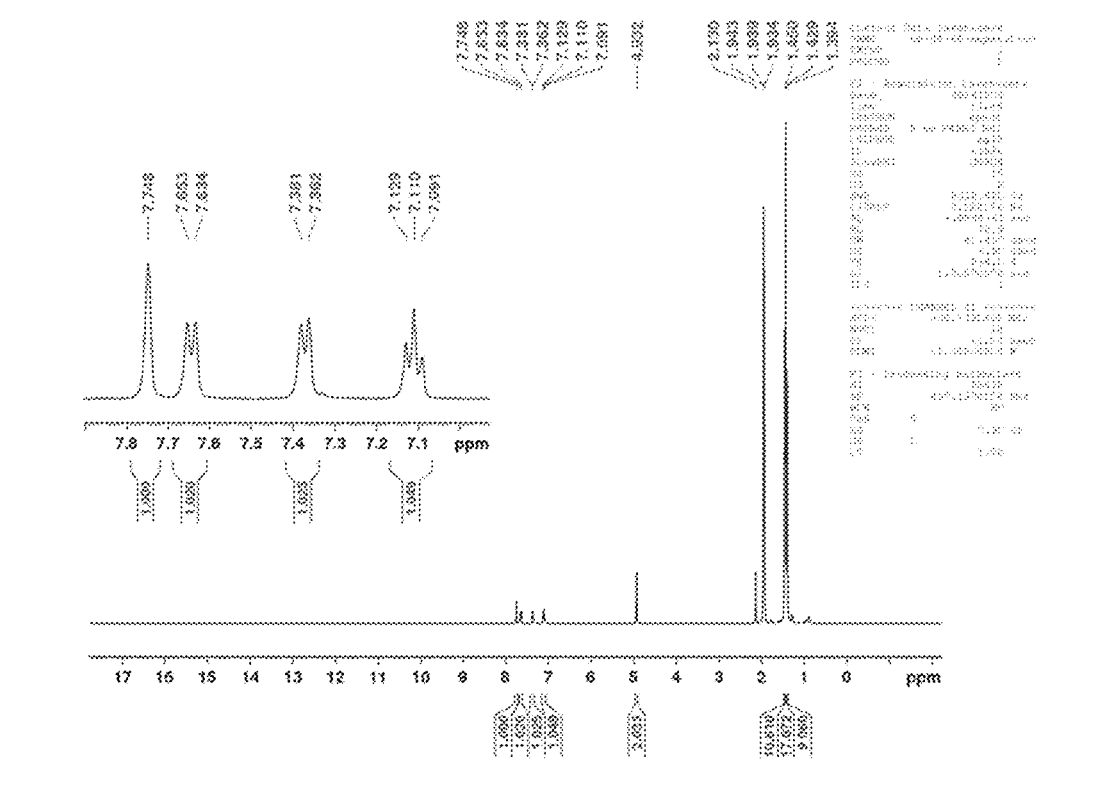
FIG. 2 depicts the 1HNMR spectrum of compound 3.
Figure 3:
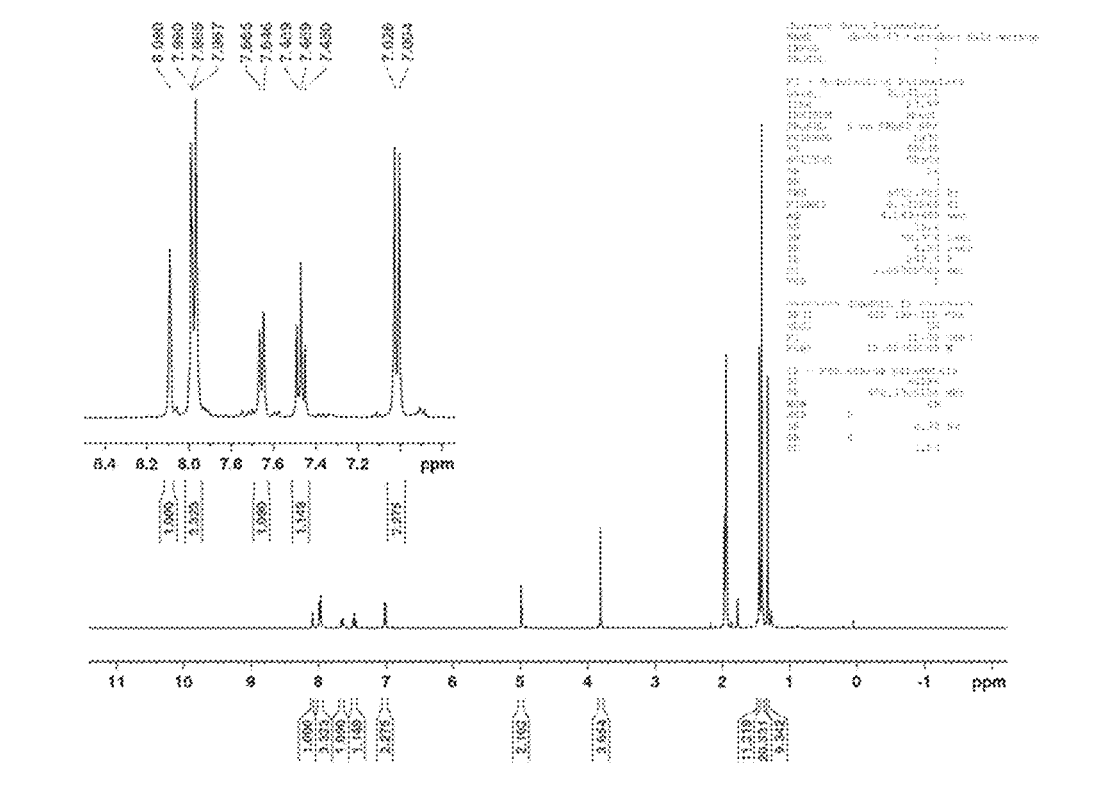
FIG. 3 depicts the 1HNMR spectrum of compound 4.
Figure 4:
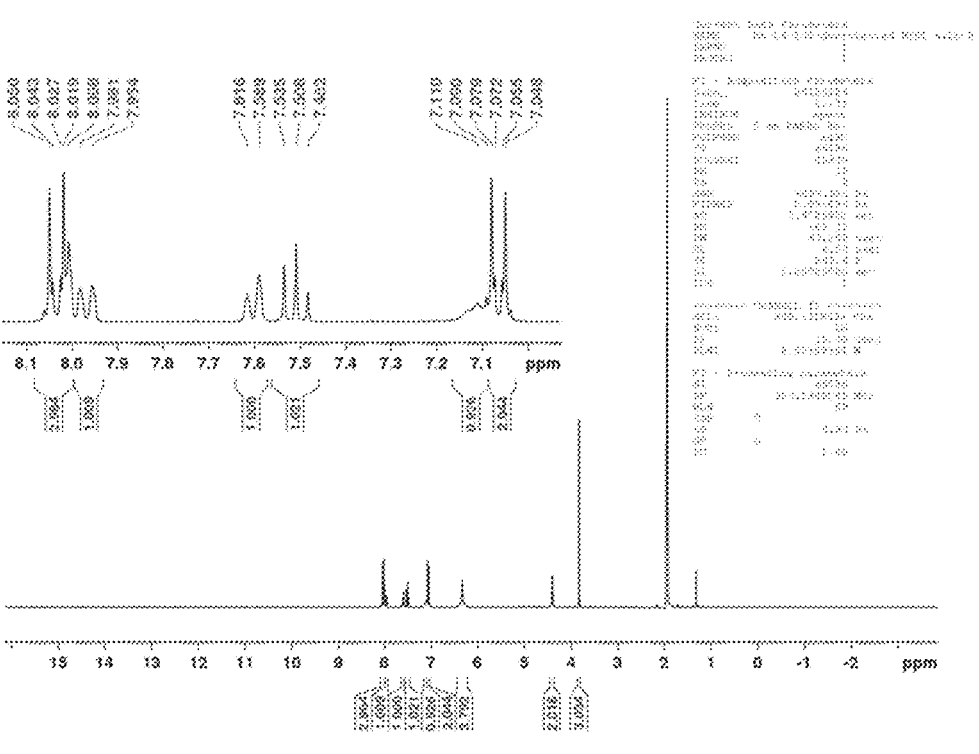
FIG. 4 depicts the 1HNMR spectrum of compound 5.

The present application provides, inter alia, a compound of formula (I):

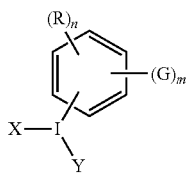

(I)

wherein:

G is -L-NH—C(—NH$_2$)(=NH$_2$)Y;
R is independently selected from the group consisting of halogen, $C_1$-$C_6$ alkyl and $C_1$-$C_6$ alkyloxy; X is selected from the group consisting of optionally substituted aryl, optionally substituted heteroaryl, and stabilized enolate; Y is absent or is an anion selected from the group consisting of bicarbonate, halide (preferably, e.g., chloride), aryl carboxylate, alkyl carboxylate (preferably, e.g., acetate, trifluoroacetate), phosphate, phosphonate, phosphonite, azide, thiocyanate, cyanate, phenoxide, arylsulfonate, alkylsulfonate, trifluoromethanesulfonate, thiolate, and stabilized enolate; L is absent or is an optionally substituted linker selected from the group consisting of alkyl, alkenyl, heteroalkyl, alkylcarbonyl, heteroalkylcarbonyl, cycloalkyl, heterocycloalkyl, aryl, and heteroaryl; n is 0-4; and m is 1-2.

In one embodiment, Y is selected from the group consisting of acetate, bicarbonate, chloride, trifluoroacetate and trifluoromethanesulfonate. In a particular embodiment, Y is trifluoromethanesulfonate.

In another embodiment, the compound of formula (I) has the structure of formula (II):

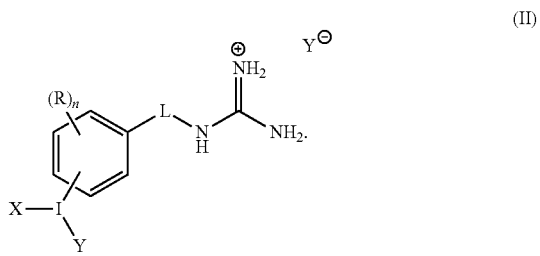

(II)

In another embodiment, X is a stabilized enolate having the structure:

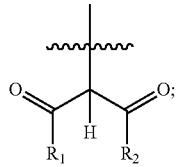

wherein $R_1$ is selected from alkyl, aryl, heteroaryl, O-alkyl, O-aryl, and O-heteroaryl; and $R_2$ is selected from alkyl, aryl, heteroaryl, O-alkyl, O-aryl, and O-heteroaryl; or wherein $R_1$ and $R_2$, and the atoms to which they are attached, form a five- or six-membered ring; and wherein Y is selected from the group consisting of acetate, bicarbonate, chloride, trifluoroacetate and trifluoromethanesulfonate. In a particular embodiment, $R_1$ and $R_2$ and the atoms to which they are attached form a six-membered ring.

In another embodiment of the compound of formula (I), X is a stabilized enolate having the structure:

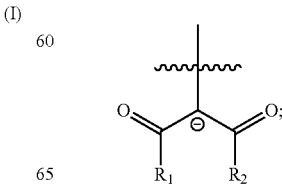

wherein R₁ is selected from alkyl, aryl, heteroaryl, O-alkyl, O-aryl, and O-heteroaryl; and R₂ is selected from alkyl, aryl, heteroaryl, O-alkyl, O-aryl, and O-heteroaryl; or wherein R₁ and R₂, and the atoms to which they are attached, form a five- or six-membered ring; and wherein Y is absent. In a particular embodiment, R₁ and R₂ and the atoms to which they are attached form a six-membered ring.

In another embodiment, the compound of formula (I) has the structure of formula (III):

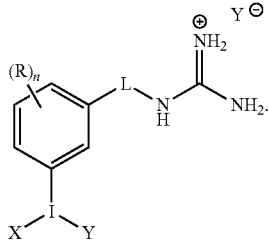

(III)

In a particular embodiment, the compound of formula (III) has the structure of formula (IV):

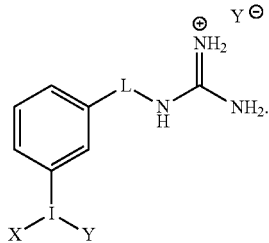

(IV)

In another particular embodiment, the compound of formula (IV) has the structure of formula (V):

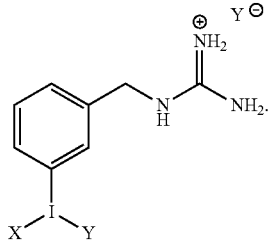

(V)

In certain embodiments of the preceding compounds, X is aryl. In other embodiments, X is 4-methoxyphenyl. In other embodiments, Y is trifluoromethanesulfonyl. In particular embodiments, X is 4-methoxyphenyl and Y is trifluoromethanesulfonyl.

In a preferred embodiment, the compound of formula (V) has the structure of compound 5:

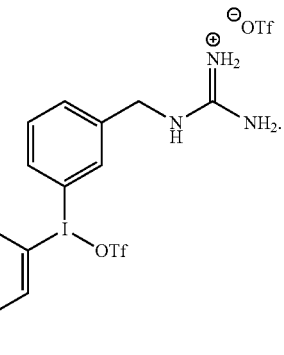

5

Methods

Also provided herein is a method of making a compound of formula (I):

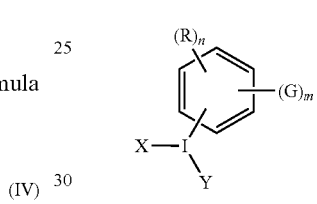

(I)

wherein: G is -L-NH—C(—NH₂)(=NH₂)Y; R is independently selected from the group consisting of halogen, $C_1$-$C_6$ alkyl and $C_1$-$C_6$ alkyloxy; X is selected from the group consisting of optionally substituted aryl, optionally substituted heteroaryl, and stabilized enolate; Y is absent or is an anion selected from the group consisting of bicarbonate, halide, aryl carboxylate, alkyl carboxylate, phosphate, phosphonate, phosphonite, azide, thiocyanate, cyanate, phenoxide, arylsulfonate, alkylsulfonate, trifluoromethanesulfonate, thiolate, and stabilized enolate; L is absent or is an optionally substituted linker selected from the group consisting of alkyl, alkenyl, heteroalkyl, alkylcarbonyl, heteroalkylcarbonyl, cycloalkyl, heterocycloalkyl, aryl, and heteroaryl; n is 0-4; and m is 1-2; the method comprising the steps of:

(1) reacting a compound of formula (Ia):

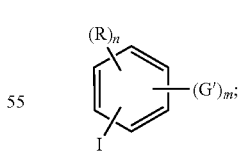

(Ia)

wherein G' is -L-NH—C(—NH₂)(=NH) or a salt thereof; and R is independently selected from the group consisting of halogen, $C_1$-$C_6$ alkyl and $C_1$-$C_6$ alkyloxy;

with a compound selected from the group consisting of (1-chloromethyl-4-fluoro-1,4-diazoniabicyclo[2.2.2]octane) bis(tetrafluoroborate), (1-fluoro-4-methyl-1,4-diazoniabicyclo[2.2.2]octane) bis(tetrafluoroborate), and optionally substituted N-fluoropyridinium tetrafluoroborate; and a compound of formula:

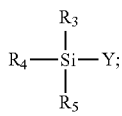

wherein $R_3$, $R_4$ and $R_5$ are optionally substituted substituents independently selected from the group consisting of alkyl, heteroalkyl, alkylaryl, aryl and heteroaryl; and wherein Y is an anion selected from the group consisting of halide, aryl carboxylate, alkyl carboxylate, phosphate, phosphonate, phosphonite, azide, thiocyanate, cyanate, phenoxide, arylsulfonate, alkylsulfonate, trifluoromethanesulfonate, thiolate, and stabilized enolate;

to obtain a compound of formula (Ib):

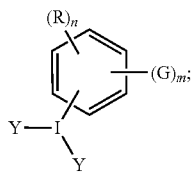

and (2) reacting the compound of formula (Ib) with a compound of formula:

X-M¹ wherein X is selected from the group consisting of optionally substituted aryl, optionally substituted heteroaryl, and stabilized enolate; and $M^1$ is a borate, stannane, silane, or zinc moiety; to obtain a compound of formula (I).

In some embodiments of the above method, $M^1$ is $Sn(R^x)_3$, $Si(R^y)_3$, $B(OR^z)_2$, or $B(X^2)_3M^2$; wherein:

each $R^x$ is, independently, $C_{1-6}$ alkyl; each $R^y$ is, independently, $C_{1-6}$ alkyl; each $R^z$ is, independently, OH or $C_{1-6}$alkoxy; or two $R^z$ groups, taken together with the oxygen atoms to which they are attached and the boron atom to which the oxygen atoms are attached, form a 5- to 6-membered heterocyclic ring, which is optionally substituted with 1, 2, 3, or 4 $C_{1-4}$ alkyl groups; each $X^2$ is, independently halogen; and $M^2$ is a counterion.

In some embodiments, the zinc moiety is a zinc halide. In a particular embodiment, the zinc halide is zinc chloride.

In some embodiments, X-M¹ is $Ar^2BF_3M^2$. In some embodiments, X-M¹ is $Ar^2BF_3K$. In some embodiments, the catalyst is trimethylsilyl trifluoroacetate.

In a preferred embodiment of the method, the compound of formula (1a) has the structure:

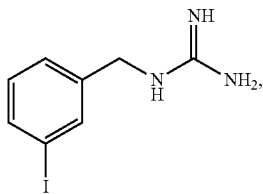 [SMILES: N=C(N)NCc1cccc(I)c1]

or a salt thereof;

the compound of formula (Ib) has the structure:

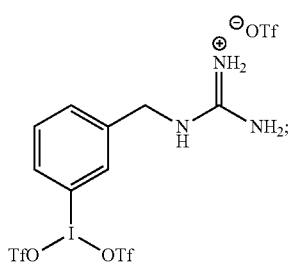 [SMILES: NC(=[NH2+])NCc1cccc(I(OS(=O)(=O)C(F)(F)F)OS(=O)(=O)C(F)(F)F)c1]

and the compound of formula (I) has the structure:

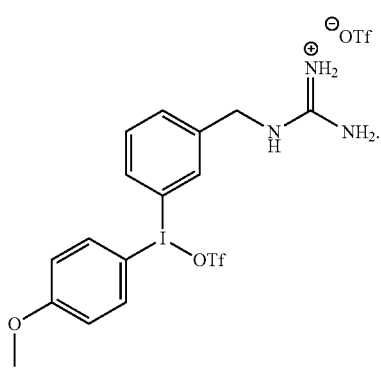 [SMILES: COc1ccc(I(OS(=O)(=O)C(F)(F)F)c2cccc(CNC(N)=[NH2+])c2)cc1]

Also provided herein is a method of making a compound of formula (X):

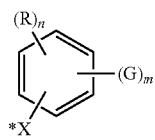

wherein: *X is selected from the group consisting of I-123, I-124, I-125, I-131, At-210 and At-211; G is -L-NH—C(—NH₂)(═NH₂)Y; R is independently selected from the group consisting of halogen, $C_1$-$C_6$ alkyl and $C_1$-$C_6$ alkyloxy; n is 0-4; and m is 1-2;

the method comprising the step of reacting a compound according to claim 1 with a source of I-123, I-124, I-125, I-131, At-210 and At-211 such that the compound of formula (X) is formed.

Suitable sources of I-123, I-124, I-125, I-131, At-210 and At-211 include, e.g., the corresponding salts of sodium, potassium, cesium and tetramethylammonium. In a preferred embodiment, the source of I-123, I-124, I-125, I-131, At-210 and At-211 is the corresponding sodium salt.

In a preferred embodiment, the compound of formula (I) has the structure of compound 5:

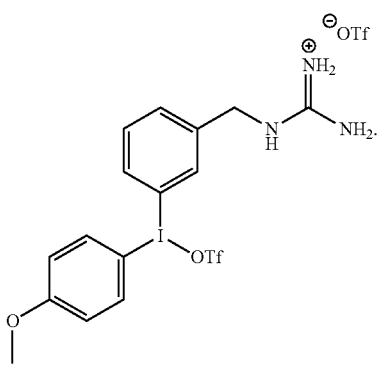

Definitions

As used herein, the term "alkyl" refers to a fully saturated branched or unbranched hydrocarbon moiety. Preferably the alkyl comprises 1 to 20 carbon atoms, 1 to 16 carbon atoms, 1 to 10 carbon atoms, more preferably 1 to 6 carbon atoms, or 1 to 4 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl and the like. Furthermore, the expression "$C_x$-$C_y$-alkyl", wherein x is 1-5 and y is 2-10 indicates a particular alkyl group (straight- or branched-chain) of a particular range of carbons. For example, the expression $C_1$-$C_4$-alkyl includes, but is not limited to, methyl, ethyl, propyl, butyl, isopropyl, tert-butyl and isobutyl. The term "alkyl carboxylate" (e.g., acetate) refers to an alkyl group that is covalently bonded to the carbonyl carbon of a carboxylate moiety. An alkyl carboxylate may further comprise a counterion (e.g., a cation). The "alkylaryl" (e.g., benzyl) refers to an alkyl group that is covalently bonded to an aryl group, as aryl is defined below.

The term "alkenyl," alone or in combination refers to a straight-chain, cyclic or branched hydrocarbon residue comprising at least one olefinic bond and the indicated number of carbon atoms. Preferred alkenyl groups have up to 8, preferably up to 6, particularly preferred up to 4 carbon atoms. Examples of alkenyl groups are ethenyl, 1-propenyl, 2-propenyl, isopropenyl, 1-butenyl, 2-butenyl, 3-butenyl, isobutenyl, 1-cyclohexenyl, 1-cyclopentenyl.

The term "alkynyl" includes unsaturated aliphatic groups analogous in length to the alkyls described above, but which contain at least one triple bond. For example, the term "alkynyl" includes straight-chain alkynyl groups (e.g., ethynyl, propynyl, butynyl, pentynyl, hexynyl, heptynyl, octynyl, nonynyl, decynyl, etc.), branched-chain alkynyl groups, and cycloalkyl or cycloalkenyl substituted alkynyl groups. The term alkynyl further includes alkynyl groups that include oxygen, nitrogen, sulfur or phosphorous atoms replacing one or more carbons of the hydrocarbon backbone. In certain embodiments, a straight chain or branched chain alkynyl group has 6 or fewer carbon atoms in its backbone (e.g., $C_2$-$C_6$ for straight chain, $C_3$-$C_6$ for branched chain). The term $C_2$-$C_6$ includes alkynyl groups containing 2 to 6 carbon atoms.

As used herein, the term "cycloalkyl" refers to saturated or unsaturated monocyclic, bicyclic or tricyclic hydrocarbon groups of 3-12 carbon atoms, preferably 3-9, or 3-7 carbon atoms. Exemplary monocyclic hydrocarbon groups include, but are not limited to, cyclopropyl, cyclobutyl, cyclopentyl, cyclopentenyl, cyclohexyl and cyclohexenyl and the like. Exemplary bicyclic hydrocarbon groups include bornyl, indyl, hexahydroindyl, tetrahydronaphthyl, decahydronaphthyl, bicyclo[2.1.1]hexyl, bicyclo[2.2.1]heptyl, bicyclo [2.2.1]heptenyl, 6,6-dimethylbicyclo[3.1.1]heptyl, 2,6,6-trimethylbicyclo[3.1.1]heptyl, bicyclo[2.2.2]octyl and the like. Exemplary tricyclic hydrocarbon groups include adamantyl and the like.

The term "cycloalkenyl" refers to a partially unsaturated cyclic hydrocarbon group containing 1 to 3 rings and 4 to 8 carbons per ring. Exemplary groups include cyclobutenyl, cyclopentenyl, and cyclohexenyl. The term "cycloalkenyl" also includes bicyclic and tricyclic groups in which at least one of the rings is a partially unsaturated, carbon-containing ring and the second or third ring may be carbocyclic or heterocyclic, provided that the point of attachment is to the cycloalkenyl group.

"Alkoxy" refers to those alkyl groups, having from 1 to 10 carbon atoms, attached to the remainder of the molecule via an oxygen atom. Alkoxy groups with 1-8 carbon atoms are preferred. The alkyl portion of an alkoxy may be linear, cyclic, or branched, or a combination thereof. Examples of alkoxy groups include methoxy, ethoxy, isopropoxy, butoxy, cyclopentyloxy, and the like. An alkoxy group can also be represented by the following formula: —$OR^i$, where $R^i$ is the "alkyl portion" of an alkoxy group.

The term "heteroalkyl," by itself or in combination with another term, means, unless otherwise stated, a stable straight or branched chain, or combinations thereof, consisting of the stated number of carbon atoms and from one to five heteroatoms, more preferably from one to three heteroatoms, selected from the group consisting of O, N, Si and S, and wherein the nitrogen and sulfur atoms may optionally be oxidized and the nitrogen heteroatom may optionally be quaternized. The heteroalkyl group is attached to the remainder of the molecule through a carbon atom or a heteroatom.

As used herein, the term "carboxyalkyl" refers to an alkyl group, as defined above, bonded to the moiety —C(=O) O— via either the carbon or the oxygen (i.e., alkyl-C(=O) O— or —O(C=O)-alkyl).

As used herein, the term "carboxyheteroalkyl" refers to a heteroalkyl group, as defined above, bonded to the moiety —C(=O)O— via either the carbon or the oxygen (i.e., alkyl-C(=O)O— or —O(C=O)-alkyl).

The term "alkylcarbonyl" refers to a group having the formula —C(O)—$R^{ii}$, wherein $R^{ii}$ is an alkyl group as defined above and wherein the total number of carbon atoms refers to the combined alkyl and carbonyl moieties. An "alkylcarbonyl" group can be attached to the remainder of the molecule via an alkyl group (i.e., -alkyl-C(O)—$R^{ii}$).

The term "alkoxycarbonyl" refers to a group having the formula —C(O)O—$R^{iii}$, wherein $R^{iii}$ is an alkyl group as defined above and wherein the total number of carbon atoms refers to the combined alkyl and carbonyl moieties. An "alkoxycarbonyl" group can be attached to the remainder of the molecule via an alkyl group (i.e., -alkyl-C(O)O—$R^{iii}$).

The term "heteroalkylcarbonyl" refers to a group having the formula —C(O)$R^{iv}$, wherein $R^{iv}$ is a heteroalkyl group as defined above and wherein the total number of carbon atoms refers to the combined alkyl and carbonyl moieties. A "heteroalkylcarbonyl" group can be attached to the remainder of the molecule via an alkyl or heteroalkyl group (i.e., -alkyl-C(O)O—$R^{iv}$ or -heteroalkyl-C(O)O—$R^{iv}$).

The term "aryl" includes aromatic monocyclic or multi-cyclic e.g., tricyclic, bicyclic, hydrocarbon ring systems consisting only of hydrogen and carbon and containing from six to nineteen carbon atoms, or six to ten carbon atoms, where the ring systems may be partially saturated. Aryl groups include, but are not limited to, groups such as phenyl, tolyl, xylyl, anthryl, naphthyl and phenanthryl. Aryl groups can also be fused or bridged with alicyclic or heterocyclic rings which are not aromatic so as to form a polycycle (e.g., tetralin). The term "aryl carboxylate" (e.g., benzoate) refers to an aryl group that is covalently bonded to the carbonyl carbon of a carboxylate moiety. An aryl carboxylate may further comprise a counterion (e.g., a cation).

The term "heteroaryl," as used herein, represents a stable monocyclic or bicyclic ring of up to 7 atoms in each ring, wherein at least one ring is aromatic and contains from 1 to 4 heteroatoms selected from the group consisting of O, N and S. Heteroaryl groups within the scope of this definition include but are not limited to: acridinyl, carbazolyl, cinnolinyl, quinoxalinyl, pyrrazolyl, indolyl, benzotriazolyl, furanyl, thienyl, benzothienyl, benzofuranyl, quinolinyl, isoquinolinyl, oxazolyl, isoxazolyl, indolyl, pyrazinyl, pyridazinyl, pyridinyl, pyrimidinyl, pyrrolyl, tetrahydroquinoline. As with the definition of heterocycle below, "heteroaryl" is also understood to include the N-oxide derivative of any nitrogen-containing heteroaryl. In cases where the heteroaryl substituent is bicyclic and one ring is non-aromatic or contains no heteroatoms, it is understood that attachment is via the aromatic ring or via the heteroatom containing ring, respectively.

The term "heterocycloalkyl" refers to a five-member to ten-member, fully saturated or partially unsaturated nonaromatic heterocylic groups containing at least one carbon and at least one heteroatom such as O, S or N. The most frequent examples are piperidinyl, morpholinyl, piperazinyl, pyrrolidinyl or pirazinyl. Attachment of a heterocycloalkyl substituent can occur via a carbon atom or via a heteroatom.

Moreover, the alkyl, alkenyl, cycloalkyl, cycloalkenyl, alkoxy, aryl, heteroaryl, and heterocycloalkyl groups described above can be "unsubstituted" or "substituted." The term "substituted" is intended to describe moieties having substituents replacing a hydrogen on one or more atoms, e.g. C, O or N, of a molecule. Such substituents can independently include, for example, one or more of the following: straight or branched alkyl (preferably $C_1$-$C_5$), cycloalkyl (preferably $C_3$-$C_8$), alkoxy (preferably $C_1$-$C_6$), thioalkyl (preferably $C_1$-$C_6$), alkenyl (preferably $C_2$-$C_6$), alkynyl (preferably $C_2$-$C_6$), heterocyclic, carbocyclic, aryl (e.g., phenyl), aryloxy (e.g., phenoxy), aralkyl (e.g., benzyl), aryloxyalkyl (e.g., phenyloxyalkyl), arylacetamidoyl, alkylaryl, heteroaralkyl, alkylcarbonyl and arylcarbonyl or other such acyl group, heteroarylcarbonyl, or heteroaryl group, $(CR'R'')_{0-3}NR'R''$ (e.g., $-NH_2$), $(CR'R'')_{0-3}CN$ (e.g., $-CN$), $-NO_2$, halogen (e.g., $-F$, $-Cl$, $-Br$, or $-I$), $(CR'R'')_{0-3}C(halogen)_3$ (e.g., $-CF_3$), $(CR'R'')_{0-3}CH(halogen)_2$, $(CR'R'')_{0-3}CH_2(halogen)$, $(CR'R'')_{0-3}CONR'R''$, $(CR'R'')_{0-3}(CNH)NR'R''$, $(CR'R'')_{0-3}S(O)_{1-2}NR'R''$, $(CR'R'')_{0-3}CHO$, $(CR'R'')_{0-3}O(CR'R'')_{0-3}H$, $(CR'R'')_{0-3}S(O)_{0-3}R'$ (e.g., $-SO_3H$, $-OSO_3H$), $(CR'R'')_{0-3}O(CR'R'')_{0-3}H$ (e.g., $-CH_2OCH_3$ and $-OCH_3$), $(CR'R'')_{0-3}S(CR'R'')_{0-3}H$ (e.g., $-SH$ and $-SCH_3$), $(CR'R'')_{0-3}OH$ (e.g., $-OH$), $(CR'R'')_{0-3}COR'$, $(CR'R'')_{0-3}$ (substituted or unsubstituted phenyl), $(CR'R'')_{0-3}(C_3-C_8$ cycloalkyl), $(CR'R'')_{0-3}CO_2R'$ (e.g., $-CO_2H$), or $(CR'R'')_{0-3}OR'$ group, or the side chain of any naturally occurring amino acid; wherein R' and R'' are each independently hydrogen, a $C_1$-$C_5$ alkyl, $C_2$-$C_5$ alkenyl, $C_2$-$C_5$ alkynyl, or aryl group.

The term "amine" or "amino" should be understood as being broadly applied to both a molecule, or a moiety or functional group, as generally understood in the art, and may be primary, secondary, or tertiary. The term "amine" or "amino" includes compounds where a nitrogen atom is covalently bonded to at least one carbon, hydrogen or heteroatom. The terms include, for example, but are not limited to, "alkyl amino," "arylamino," "diarylamino," "alkylarylamino," "alkylaminoaryl," "arylaminoalkyl," "alkaminoalkyl," "amide," "amido," and "aminocarbonyl." The term "alkyl amino" comprises groups and compounds wherein the nitrogen is bound to at least one additional alkyl group. The term "dialkyl amino" includes groups wherein the nitrogen atom is bound to at least two additional alkyl groups. The term "arylamino" and "diarylamino" include groups wherein the nitrogen is bound to at least one or two aryl groups, respectively. The term "alkylarylamino," "alkylaminoaryl" or "arylaminoalkyl" refers to an amino group which is bound to at least one alkyl group and at least one aryl group. The term "alkaminoalkyl" refers to an alkyl, alkenyl, or alkynyl group bound to a nitrogen atom which is also bound to an alkyl group.

The term "amide," "amido" or "aminocarbonyl" includes compounds or moieties which contain a nitrogen atom which is bound to the carbon of a carbonyl or a thiocarbonyl group. The term includes "alkaminocarbonyl" or "alkylaminocarbonyl" groups which include alkyl, alkenyl, aryl or alkynyl groups bound to an amino group bound to a carbonyl group. It includes arylaminocarbonyl and arylcarbonylamino groups which include aryl or heteroaryl moieties bound to an amino group which is bound to the carbon of a carbonyl or thiocarbonyl group. The terms "alkylaminocarbonyl," "alkenylaminocarbonyl," "alkynylaminocarbonyl," "arylaminocarbonyl," "alkylcarbonylamino," "alkenylcarbonylamino," "alkynylcarbonylamino," and "arylcarbonylamino" are included in term "amide." Amides also include urea groups (aminocarbonylamino) and carbamates (oxycarbonylamino).

In a particular embodiment of the invention, the term "amine" or "amino" refers to substituents of the formulas $N(R^8)R^9$, $CH_2N(R^8)R^9$ and $CH(CH_3)N(R^8)R^9$, wherein $R^8$ and $R^9$ are each, independently, selected from the group consisting of H and $(C_1-C_4$-alkyl$)_{0-1}$G, wherein G is selected from the group consisting of COOH, H, $PO_3H$, $SO_3H$, Br, Cl, F, $O-C_{1-4}$-alkyl, $S-C_{1-4}$-alkyl, aryl, $C(O)OC_1$-$C_6$-alkyl, $C(O)C_1$-$C_4$-alkyl-COOH, $C(O)C_1$-$C_4$-alkyl and $C(O)$-aryl.

The description of the disclosure herein should be construed in congruity with the laws and principals of chemical bonding. For example, it may be necessary to remove a hydrogen atom in order accommodate a substituent at any given location. Furthermore, it is to be understood that definitions of the variables (i.e., "R groups"), as well as the bond locations of the generic formulae of the invention (e.g., Formulas (I)-(X)), will be consistent with the laws of chemical bonding known in the art. It is also to be understood that all of the compounds of the invention described above will further include bonds between adjacent atoms and/or hydrogens as required to satisfy the valence of each atom. That is, bonds and/or hydrogen atoms are added to provide the following number of total bonds to each of the following types of atoms: carbon: four bonds; nitrogen: three bonds; oxygen: two bonds; and sulfur: two-six bonds.

The compounds of this invention may include asymmetric carbon atoms. It is to be understood accordingly that the isomers arising from such asymmetry (e.g., all enantiomers, stereoisomers, rotamers, tautomers, diastereomers, or racemates) are included within the scope of this invention. Such isomers can be obtained in substantially pure form by classical separation techniques and by stereochemically controlled synthesis. Furthermore, the structures and other compounds and moieties discussed in this application also include all tautomers thereof. Compounds described herein may be obtained through art recognized synthesis strategies.

It will also be noted that the substituents of some of the compounds of this invention include isomeric cyclic structures. It is to be understood accordingly that constitutional isomers of particular substituents are included within the scope of this invention, unless indicated otherwise. For example, the term "tetrazole" includes tetrazole, 2H-tetrazole, 3H-tetrazole, 4H-tetrazole and 5H-tetrazole.

The term "protected", as used herein in reference to a chemical moiety (e.g., a guanidine moiety), means that the particular functional moiety, or constituent atoms thereof (e.g., nitrogen atoms), is temporarily blocked so that a reaction can be carried out selectively at another reactive site in a multifunctional compound. Such temporary blocking is accomplished using a "protecting group", i.e., a chemical moiety that is covalently bonded to the "protected" moiety or atom. Nitrogen protecting groups include, but are not limited to, carbamates (including methyl, ethyl and substituted ethyl carbamates (e.g., Troc), to name a few) amides, cyclic imide derivatives, N-Alkyl and N-Aryl amines, imine derivatives, and enamine derivatives, to name a few. Certain other exemplary protecting groups are detailed herein, however, it will be appreciated that the present invention is not intended to be limited to these protecting groups; rather, a variety of additional equivalent protecting groups can be readily identified using the above criteria and utilized in the present invention. Additionally, a variety of protecting groups are described in "Protective Groups in Organic Synthesis" Third Ed. Greene, T. W. and Wuts, P. G., Eds., John Wiley & Sons, New York: 1999, the entire contents of which are hereby incorporated by reference.

It will be appreciated that the compounds, as described herein, may be substituted with any number of substituents or functional moieties. In general, the term "substituted" whether preceded by the term "optionally" or not, and substituents contained in formulas of this invention, refer to the replacement of hydrogen radicals in a given structure with the radical of a specified substituent. When more than one position in any given structure may be substituted with more than one substituent selected from a specified group, the substituent may be either the same or different at every position. As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. For purposes of this invention, heteroatoms such as nitrogen may have hydrogen substituents and/or any permissible substituents of organic compounds described herein which satisfy the valencies of the heteroatoms. Furthermore, this invention is not intended to be limited in any manner by the permissible substituents of organic compounds. Combinations of substituents and variables envisioned by this invention are preferably those that result in the formation of stable compounds.

EXAMPLES

Example 1

Unprotected Synthesis of Compound 5

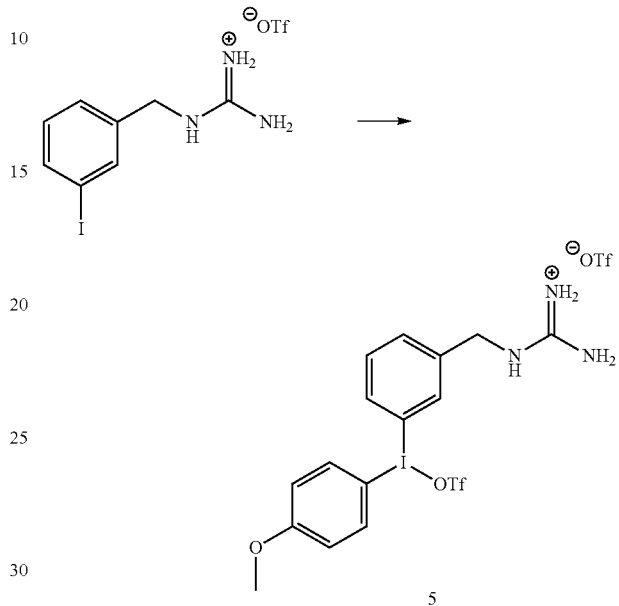

Under an atmosphere of dry nitrogen, (3-iodobenzyl) guanidinium triflate (3.0 mmol), Selectfluor™ (3.9 mmol, 1.39 g, 1.3 eq.) and 15 mL of dry CH3CN are introduced to an oven-dried Schlenk flask. A solution of TMSOAc (7.8 mmol, 1.03 g, 2.6 eq.) in dry $CH_3CN$ (5 mL) is added by syringe dropwise with stirring. This colorless mixture is stirred at room temperature for 24 h. Solid potassium (4-methoxyphenyl)trifluoroborate (0.64 g, 3.0 mmol, 1.0 equiv.) is added directly to the flask against a flow of nitrogen. Once the added solid is dissolved and a homogeneous mixture is obtained (3 minutes), a solution of TMSOTf (0.67 g, 2.7 mmol, 0.9 eq.) in 10.0 mL of dry $CH_3CN$ is added dropwise by syringe and the mixture is allowed to stir at room temperature for 10 min. The solvents are removed under reduced pressure and 100 mL of 0.1 M acetate buffer (pH=5) is added. The mixture is extracted with $CH_2Cl_2$ (3×50 mL). The combined organic layers are added to a separatory funnel and washed with water (50 mL), and the wash water is extracted further (2×50 mL) with $CH_2Cl_2$. The combined organic extracts are dried over sodium sulfate, filtered, and the solvent is removed by rotary evaporation. The residue is placed under dynamic vacuum, and the solid obtained is dissolved in 10.0 mL ethyl acetate and added dropwise to a mixture of MTBE and hexane (1:4) to precipitate the diaryliodonium triflate product. The obtained solid is dissolved in 1 mL acetonitrile/water (9:1 by volume) solution and passed down an Amberlite IRA-400 ion exchange column (triflate counterion). After removal of the solvents under reduced pressure, the purified iodonium triflate product, compound 5, is obtained as a colorless solid.

Example 2

Radioiodination of Compound 5

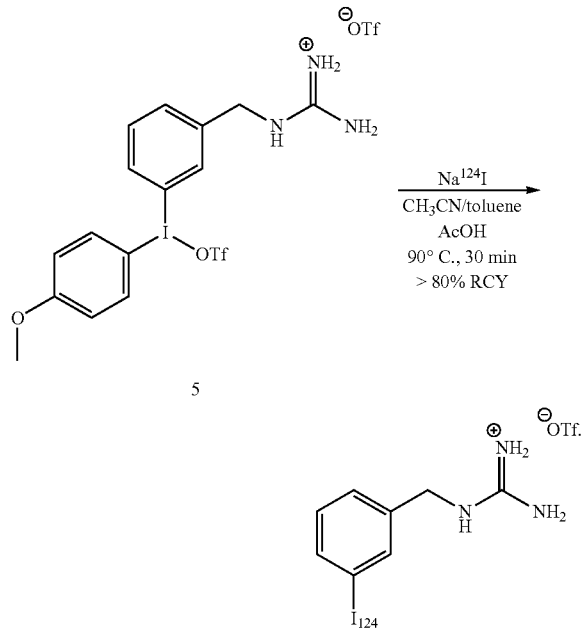

(1) Preparation of Iodide Solution:

Aqueous $Na^{124}I$ was dissolved in 0.1 M NaOH. 1 uL of $Na^{124}I$ (approximately 1 mCi) was added to a reaction vial along with 1 uL of 1.0 M AcOH to prepare an acidic, slightly buffered solution. The initial activity was then recorded for later calculations. Because the volume of water was so small, initial drying of the Na*I solution was not required. (For larger scale reactions that involve more water, an azeotropic drying procedure with 400 uL of $CH_3CN$ is performed before the labeling step.

(2) Labeling:

5 mg of the protected diaryliodonium precursor was dissolved in 400 uL of $CH_3CN$. The mixture was allowed to stand for 10 minutes to make certain all of the crystalline substrate had dissolved. The dissolved precursor was added to the reaction vial and then the solution was evaporated with a stream of dry argon at 90° C. (approximately two minutes). After the solvent was removed completely, 125 uL of $CH_3CN$ was added (with shaking or stirring) to dissolve the salts. Toluene (125 uL) was added and the solution was heated at 90° C. for 30 minutes before the solvent was evaporated with a stream of dry argon.

(3) Semipreparative HPLC Purification:

The dry residue from the reaction mixture was dissolved in chromatography buffer (50% acetonitrile/50% 20 mM ammonium acetate) and was injected into a semipreparative HPLC column (Alltech Econosphere C18; 250×4.6 mm) and eluted at 7.3 minutes at a flow rate of 1.5 mL/minute.

(4) Post HPLC Isolation:

The collected fraction was diluted with 20 mL $H_2O$ and trapped on a second C18 sep pak. The cartridge was rinsed with distilled water, blown dry, and the product was eluted in 0.8 mL of ethanol. $^{124}I$-MIBG was isolated from this procedure in 90% radiochemical yield from this procedure.

Example 3

Synthesis of Compound 5

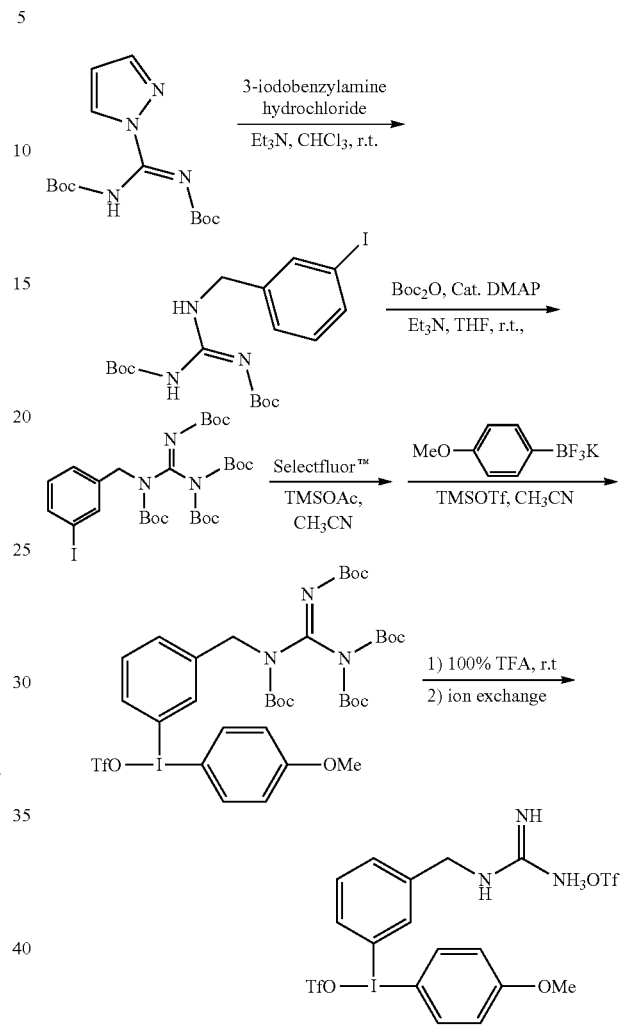

(1) N',N''-bis(tert-butoxycarbonyl)-N-3-iodobenzyl-guanidine (Compound 2)

To a solution of 3-iodobenzylamine hydrochloride (2.96 g, 11 mmol, 1.1 equiv.) and $Et_3N$ (1.7 mL, 12 mmol, 1.2 equiv.) in 50 mL of chloroform was added N,N'-bis(t-butoxycarbonyl)-1H-pyrazole-1-carboxamidine (3.10 g, 10 mmol, 1.0 equiv.) at room temperature. After the mixture was stirred for 4 h, it was treated with water and the organic layer was separated. The water layer was extracted once with $CH_2Cl_2$ and the combined organic layers were washed with water, dried over anhydrous Na$_2$SO$_4$, filtered, and concentrated. The obtained product (colorless solid: 3.80 g, 80%) was sufficiently pure to be carried forward. $^1$H NMR (400 MHz, CDCl$_3$) δ 11.53 (brs, 1 H), 8.59 (brs, 1 H), 7.67 (s, 1 H), 7.63 (d, J=7.6 Hz, 1 H), 7.28 (d, J=7.6 Hz, 1 H), 7.08 (t, J=7.6 Hz, 1 H), 4.57 (d, J=5.6 Hz, 1 H), 1.52 (s, 9 H), 1.49 (s, 9 H); $^{13}$C NMR (100 MHz, CDCl$_3$) δ 161.9, 154.5, 151.6, 138.2, 135.3, 135.1, 128.8, 125.5, 92.9, 81.7, 77.9, 42.5, 26.7, 26.5; HRMS (ESI) Calcd for C$_{18}$H$_{26}$N$_3$O$_4$INa (M+Na)$^+$: 498.0866; Found: 498.0868.

(2) 3-((1,2,3,3-Tetrakis(tert-butoxycarbonyl)guanidino)methyl)iodobenzene (Compound 3)

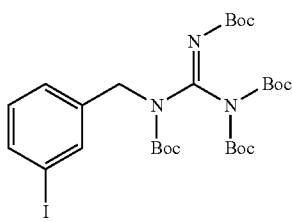

DMAP (122 mg, 1.0 mmol, 0.1 equiv.) was added to a solution of N',N''-bis(tert-butoxycarbonyl)-N-3-iodobenzyl-guanidine (3.80 g, 8 mmol, 1.0 equiv.) and Et$_3$N (4.2 mL, 30 mmol, 3.0 equiv.) in THF (50 mL). A solution of di-tert-butyldicarbonate (4.36 g, 20 mmol, 2.0 equiv.) in THF (40.0 mL) was added slowly (over approximately 5 h) and the solution was stirred overnight at room temperature. An additional aliquot of di-tert-butyldicarbonate (2.18 g, 10 mmol, 1.0 equiv.) in THF (20.0 mL) was added to drive the reaction to completion. The mixture was concentrated in vacuo and the residue was purified by silica gel chromatography (EtOAc/hexane, 1:10) to give the title compound as colorless solid (5.12 g, 95% yield). $^1$H NMR (400 MHz, CD$_3$CN) δ 7.75 (s, 1 H), 7.64 (d, J=7.6 Hz, 1 H), 7.37 (d, J=7.6 Hz, 1 H), 7.11 (t, J=7.6 Hz, 1 H), 4.93 (s, 2 H), 1.45 (s, 9 H), 1.43 (s, 18 H), 1.39 (s, 9 H). $^{13}$C NMR (700 MHz, CDCl$_3$) δ 157.4, 151.2, 147.2, 145.1, 140.2, 136.3, 136.2, 130.3, 126.9, 93.6, 84.1, 83.6, 81.8, 49.4, 27.2; HRMS (ESI) Calcd for C$_{28}$H$_{42}$IN$_3$O$_8$Na (M+Na)$^+$: 698.1914; found: 698.1901.

(3) (4-methoxyphenyl)(3-((1,2,3,3-tetrakis(tert-butoxycarbonyl)guanidino)methyl)phenyl)iodonium trifluoromethanesulfonate (Compound 4)

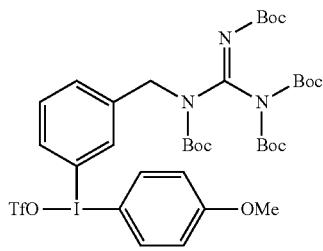

In a N$_2$ charged glovebox, a solution of TMSOAc (15.6 mmol, 2.06 g, 2.6 eq.) in 15 mL of dry CH$_3$CN was added dropwise to a solution of Selectfluor™ (7.8 mmol, 2.76 g, 1.3 eq.) in 15 mL of dry CH$_3$CN. The resulting colorless mixture was then added slowly (dropwise) to a solution of 3-((1,2,3,3-tetrakis(tert-butoxycarbonyl)guanidino)methyl) iodobenzene (6.0 mmol, 4.05 g, 1.0 eq.) in 20 mL of dry CH$_3$CN. The mixture was stirred at room temperature for 33 h before potassium 4-methoxyphenyltrifluoroborate (1.28 g, 6.0 mmol, 1.0 equiv.) was added. Immediately thereafter, a solution of TMSOTf (1.20 g, 5.4 mmol, 0.90 eq.) in 10.0 mL of dry CH$_3$CN was added slowly (dropwise), and the mixture was allowed to stand at room temperature for 30 minutes. The acetonitrile was removed by rotary evaporation, 100 mL of deionized water was added, and the mixture was extracted (3×50 mL) with CH$_2$Cl$_2$. The combined organic extracts were washed with water (100 mL) and the aqueous layer was extracted (2×50 mL) with CH$_2$Cl$_2$ again. The combined organic extracts were dried over sodium sulfate, filtered, and concentrated in vacuo. The residue was washed with hexane to give the diaryliodonium triflate. This compound was dissolved in 1 mL acetonitrile/water (9:1 by volume) solution and slowly passed down an Amberlite IRA-400 ion exchange column (triflate counterion). After removal of the solvents under reduced pressure, the iodonium triflate product (3.80 g, 68% yield) of was obtained as a colorless solid. $^1$H NMR (400 MHz, CD$_3$CN) δ 8.09 (s, 1 H), 7.98 (d, J=9.2 Hz, 2 H), 7.97 (d, J=7.6 Hz, 1 H), 7.66 (d, J=7.6 Hz, 1 H), 7.47 (t, J=7.6 Hz, 1 H), 7.01 (d, J=8.8 Hz, 1 H), 4.99 (s, 2 H), 3.81 (s, 3 H), 1.45 (s, 9 H), 1.41 (s, 18 H), 1.33 (s, 9 H); $^{13}$C NMR (176 MHz, CDCl$_3$) δ 163.1, 157.2, 151.0, 147.4, 145.0, 142.2, 137.4, 133.9, 133.8, 132.0, 131.3, 118.0, 114.9, 102.7, 84.5, 83.9, 82.1, 55.7, 49.4, 27.3, 27.2, 27.2, 27.1, 26.2; HRMS (ESI) Calcd for C$_{35}$H$_{49}$IN$_3$O$_9$(M−OTf)$^+$: 782.2514; found: 782.2491.

(4) (3-(Guanidinomethyl)phenyl)(4-methoxyphenyl)iodonium trifluoromethanesulfonate trifluoromethanesulfonic acid (Compound 5)

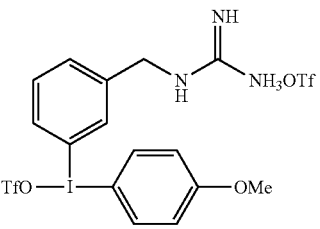

The above tetraboc-protected diaryliodonium salt (1.28 g, 1.37 mmol) was treated with trifluoroacetic acid (5 mL) and stirred at room temperature for overnight. The TFA was removed under reduced pressure, and the resulting residue was washed with ether to give the diaryliodonium triflate. This compound was dissolved in 1 mL acetonitrile/water (9:1 by volume) solution and slowly passed down an Amberlite IRA-400 ion exchange column (triflate counterion). After removal of the solvents under reduced pressure, the iodonium triflate product (0.80 g, 86% yield) of was obtained as a colorless solid (highly hygroscopic). $^1$H NMR (300 MHz, CD$_3$CN) δ 8.04 (d, J=9.3 Hz, 2 H), 8.01 (s, 1 H), 7.97 (d, J=8.1 Hz, 1 H), 7.60 (d, J=8.1 Hz, 1 H), 7.51 (t, J=8.1 Hz, 1 H), 7.11 (brs, 1 H), 7.07 (d, J=9.3 Hz, 2 H), 6.34 (brs, 4 H), 4.42 (d, J=6.3 Hz, 2 H), 3.84 (s, 3 H); $^{13}$C NMR (175 MHz, CD$_3$CN) δ 163.4, 157.1, 140.8, 137.8, 134.1, 133.2, 132.3, 131.5, 118.2, 114.2, 101.4, 55.7, 43.9; $^{19}$F NMR (CD$_3$CN, 376 MHz): δ −79.4 (s, 3 F).

Example 4

General Procedure for the Radioiodination of NHS-ester and Maleimide Conjugation Reagents A diaryliodonium salt precursor (5 mg) was dissolved in 2.5 mL of dry acetonitrile. An aqueous solution of NaI (in which the isotope of iodide was either $^{123}$I, $^{124}$I, $^{125}$I, or $^{131}$I) was counted and added to 400 μL of dry acetonitrile. If the initial NaI source was basic, 10 equivalents of acetic acid (per equivalent of NaOH) was added, and the solution was mixed and evaporated to dryness at 80° C. An aliquot of the precursor solution (400 μL) was added to the dried NaI and the resulting mixture was again evaporated to dryness. Dry acetonitrile (125 μL) was added to dissolve the residue, and 125 μL of dry toluene was added to adjust the solvent polarity. The reaction mixture was heated at 95° C. for 1 hour. Monitoring by radio TLC showed that radioiodide incorporation was 50-94% after 1 hour. Sep-pak purification was performed to remove the residual radioiodide and starting material. Final purification and/or quality control was performed by reverse phase HPLC.

The invention claimed is:

1. A compound of formula (I):

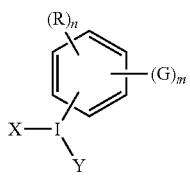

(I)

wherein:
G is -L-NH—C(—NH$_2$)(=NH$_2$)Y;
R is independently selected from the group consisting of halogen, C$_1$-C$_6$ alkyl and C$_1$-C$_6$ alkyloxy;
X is optionally substituted aryl;
Y is absent or is an anion selected from the group consisting of bicarbonate, halide, aryl carboxylate, alkyl carboxylate, phosphate, phosphonate, phosphonite, azide, thiocyanate, cyanate, phenoxide, arylsulfonate, alkylsulfonate, trifluoromethanesulfonate, thiolate, and stabilized enolate;
L is absent or is an optionally substituted linker selected from the group consisting of alkyl, alkenyl, heteroalkyl, alkylcarbonyl, heteroalkylcarbonyl, cycloalkyl, heterocycloalkyl, or aryl;
n is 0-4; and
m is 1-2.

2. The compound of claim 1, wherein m is 1 and the compound of formula (I) has the structure of formula (II):

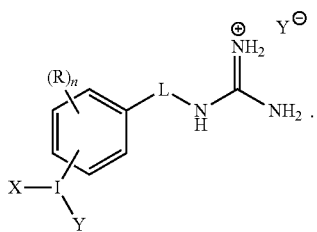

(II)

3. The compound of claim 1, wherein X is aryl.

4. The compound of claim 1, wherein the X is 4-methoxyphenyl.

5. The compound of claim 1, wherein Y is trifluoromethylsulfonate.

6. The compound of claim 2 having the structure of formula (III):

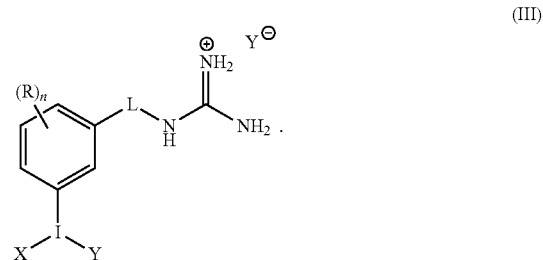

(III)

7. The compound of claim 6, having the structure of formula (IV):

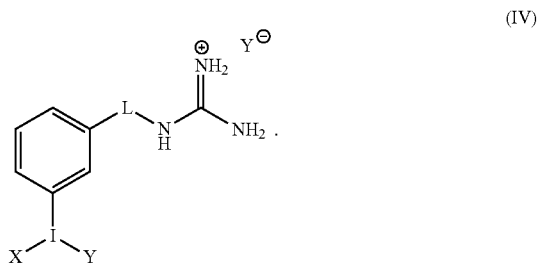

(IV)

8. The compound of claim 7, having the structure of formula (V):

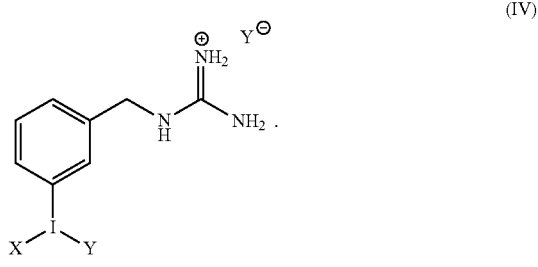

(IV)

9. The compound of claim 6, wherein X is aryl.
10. The compound of claim 6, wherein X is 4-methoxyphenyl.
11. The compound of claim 6, wherein each instance of Y is trifluoromethanesulfonyl.
12. The compound of claim 1, wherein X is 4-methoxyphenyl and each instance of Y is trifluoromethanesulfonyl.
13. A method of making a compound of formula (I):

(I)

wherein:

G is -L-NH—C(—NH$_2$)(=NH$_2$)Y;

R is independently selected from the group consisting of halogen, C$_1$-C$_6$ alkyl and C$_1$-C$_6$ alkyloxy;

X is optionally substituted aryl;

Y is absent or is an anion selected from the group consisting of bicarbonate, halide, aryl carboxylate, alkyl carboxylate, phosphate, phosphonate, phosphonite, azide, thiocyanate, cyanate, phenoxide, arylsulfonate, alkylsulfonate, trifluoromethanesulfonate, thiolate, and stabilized enolate;

L is absent or is an optionally substituted linker selected from the group consisting of alkyl, alkenyl, heteroalkyl, alkylcarbonyl, heteroalkylcarbonyl, cycloalkyl, heterocycloalkyl, and aryl;

n is 0-4; and m is 1-2;

the method comprising the steps of:

(1) reacting a compound of formula (Ia):

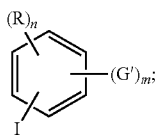

wherein G' is -L-NH—C(—NH$_2$)(=NH) or a salt thereof; and R is independently selected from the group consisting of halogen, C$_1$-C$_6$ alkyl and C$_1$-C$_6$ alkyloxy;

with a compound selected from the group consisting of (1-chloromethyl-4-fluoro-1,4-diazoniabicyclo[2.2.2]octane) bis(tetrafluoroborate), (1-fluoro-4-methyl-1,4-diazoniabicyclo[2.2.2]octane) bis(tetrafluoroborate), and optionally substituted N-fluoropyridinium tetrafluoroborate; and a compound of formula:

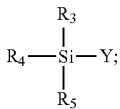

wherein R$_3$, R$_4$ and R$_5$ are optionally substituted substituents independently selected from the group consisting of alkyl, heteroalkyl, alkylaryl, aryl and heteroaryl; and wherein Y is an anion selected from the group consisting of halide, aryl carboxylate, alkyl carboxylate, phosphate, phosphonate, phosphonite, azide, thiocyanate, cyanate, phenoxide, arylsulfonate, alkylsulfonate, trifluoromethanesulfonate, thiolate, and stabilized enolate;

to obtain a compound of formula (Ib):

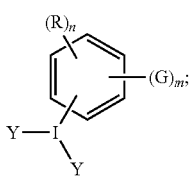

and (2) reacting the compound of formula (Ib) with a compound of formula:

X-M$^1$ wherein X is selected from the group consisting of optionally substituted aryl, optionally substituted heteroaryl, and stabilized enolate; and M$^1$ is a borate, stannane, silane, or zinc moiety;

to obtain a compound of formula (I).

14. The compound of claim 1 having the structure:

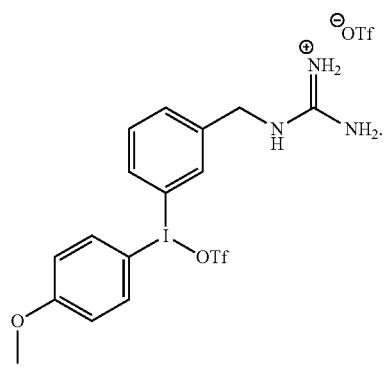 [SMILES: COc1ccc(I(OS(=O)(=O)C(F)(F)F)c2cccc(CNC(N)=[NH2+])c2)cc1 ; "OTf"]

15. A compound of formula (I):

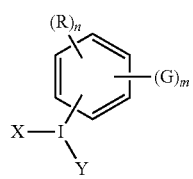

wherein:

G is -L-NH—C(—NH$_2$)(=NH$_2$)Y;

R is independently selected from the group consisting of halogen, C$_1$-C$_6$ alkyl and C$_1$-C$_6$ alkyloxy;

X is optionally substituted heteroaryl;

Y is absent or is an anion selected from the group consisting of bicarbonate, halide, aryl carboxylate, alkyl carboxylate, phosphate, phosphonate, phosphonite, azide, thiocyanate, cyanate, phenoxide, arylsulfonate, alkylsulfonate, trifluoromethanesulfonate, thiolate, and stabilized enolate;

L is absent or is an optionally substituted linker selected from the group consisting of alkyl, alkenyl, heteroalkyl, alkylcarbonyl, heteroalkylcarbonyl, cycloalkyl, heterocycloalkyl, or aryl;

n is 0-4; and m is 1-2.

* * * * *